US008338098B2

(12) United States Patent
Khatib et al.

(10) Patent No.: US 8,338,098 B2
(45) Date of Patent: Dec. 25, 2012

(54) METHODS AND COMPOSITIONS FOR IMPROVED CATTLE LONGEVITY AND MILK PRODUCTION

(75) Inventors: Hasan Khatib, Madison, WI (US); Wen Huang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 940 days.

(21) Appl. No.: 12/267,104

(22) Filed: Nov. 7, 2008

(65) Prior Publication Data

US 2009/0216074 A1 Aug. 27, 2009

Related U.S. Application Data

(60) Provisional application No. 60/986,241, filed on Nov. 7, 2007.

(51) Int. Cl.
*C12Q 1/68* (2006.01)
*C07H 21/02* (2006.01)
*C07H 21/04* (2006.01)
(52) U.S. Cl. ....... 435/6.11; 435/6.1; 536/23.1; 536/23.5
(58) Field of Classification Search .................. None
See application file for complete search history.

(56) References Cited

U.S. PATENT DOCUMENTS 5,614,364 A * 3/1997 Tuggle et al. ................ 435/6.12

FOREIGN PATENT DOCUMENTS

WO WO 95/11995 A1 * 5/1995

OTHER PUBLICATIONS

GenBank Accession NM_174579.2 (Feb. 8, 2006).*
Kinghorn et al., Potential Genetics in dairy Cattle with Gamete Harvesting and In Vitro Fertilization, Journal of Dairy Science, 2004, vol. 74, No. 2, pp. 611-622. Abstract.
Zakizadeh et al., Polymorphism of the Bovine POU1F1 Gene: Allele Frequencies and Effects on Milk Production in Three Iranian Native Breeds and Holstein Cattle of Iran, Pakistan Journal of Biological Science, 2007, vol. 10, No. 15, pp. 2575-2578. Abstract, Introduction.
Lee W. Young International Application No. PCT/US 08/82811 International Search Report under PCT Rule 44.1 Date of search: Jun. 19, 2009 p. 3 International Searching Authority ISA/US.

* cited by examiner

*Primary Examiner* — Juliet Switzer
*Assistant Examiner* — Joseph G Dauner
(74) *Attorney, Agent, or Firm* — Kening Li; Pinsent Masons LLP

(57) ABSTRACT

A single nucleotide polymorphic site at position 10793 of the bovine POU1F1 gene is associated with improved longevity and milk product traits. Disclosed are nucleic acid molecules, kits, methods of genotyping and marker assisted bovine breeding methods.

7 Claims, 6 Drawing Sheets

```
   1 ttctccgttt ctattctttt gtgggaatga gttgccaacc ttttacttcg actgatacct
  61 ttatacctct gaattctgag tcttctgcaa ctctgcctct gataatgcat cccagtgctg
 121 cggagtgcct accggtctcc aaccacgcca ccaacgtgat gtccacaggt actaacttca
 181 ataacagtct acatgcggct gcgccttaag atatcaggat gggtgctttg aatcttgcta
 241 gtttagaatc tcattttaaa aaaaatttta atgtgtatta agttaaatat tcaggatatt
 301 aaagaagaca aaatgcctaa gaaatattc aagaaatatt agtaagtgta gtaatttcaa
 361 gtattgttga ttttattata aaacctgtct tctatacaag taaacagtga gtctgaaaac
 421 cactctatgc aaacatgtat gcataaagag taaaactaaa aaaatagtgt aaaataattt
 481 aaaaggtgat ttttttttcct cttagagatt tatttggttt ttagattaca tttactacca
 541 tgtctaaaaa atgccgtaca cctctgagta aacacaactg aatgattcct gataccaaca
 601 acagtgggtt tcaaagaata aaataattag atgtttaaat acactttatt cagatggtaa
 661 agaatctccc tacaatgcag gagacccagg tctgatccct gggtcaggaa gatcccatgg
 721 agaagggaat ggcaacccac tccactattt ttgcctggcg aagtccaagg acagaggagc
 781 ctggcaggtt acagtccatg gggttgcaaa gagtcggaca caactgaacg actaacactt
 841 tcactttaaa tacacttaac ttctttagaa taattaaaaa ctcagaaacc aagtctagag
 901 gcaatataat atttatttgt ttattttttaa aactttttat tttatattgg agtatagcca
 961 gttaacaatg ttgtgatatt tcagatgga cagcagagga attcagccat acatacacta
1021 tatccttttt tacccaaact cccctcccat ctaggctaga ggcaatataa tatttagaat
1081 ccatgaactg atttgaatct tttcaagatt tagttctgaa gagatttcaa cctttaatca
1141 agttttata ttttcttata aactttctt agatgaaaat taaaattaat tcaaatatat
1201 tgtctcaaac acaaccaagt aaataaatat gttttgttaa tgtgtctaattttactcag
1261 taacaaaggg ttttgattaa taaacaatgt cttgggtaaa tgtctgttta atagcactt
1321 tcacttgtaa agcaatctaa atatgagcta aatttataa atttaaaaat caatttgagt
1381 tgacacattt atatgccaat ttaaaatatt ttagccttat attttgttaa aattaagcag
1441 ctttgaaagt tatatgtaag tttggtatta atctttaaca gaattttcaa atatctgaag
1501 atcatattat ctagatttgg ggaaaattat taatgtagag atgttttta tctactgaag
1561 agtctcagaa tttaattaaa catatgctga tgcaaatatc ctcaaacatg gttttaaaaa
1621 aaagtaataa agtatttta tgaagaggtg tggtataaat aaatttaaac aattatcaca
1681 tattgttgta ttgttcagtc gctaagtctg aactctgcaa ctctttgcaa ccccatggac
1741 tgcagcatgc cagacttccc tgtccttcac tatctcctgg actcttccca tacaattatc
1801 acatagctaa ttgtgtattt taaataatgg acatttaaat agattgagaa tgagaaggat
1861 agtgcatttt tgcataatat actgtatgtg gatagtattt ggctagaata aaaattggaa
1921 ttgaggttaa aattaagcag gtttaagctc aaaaccctat ttatttaaaa aaaaataaaa
1981 gtaaataaat aatgtatcta gtaaattagc ttgtcattta tatgacttcc ccaaatcagc
2041 aaaacaaaag aatttaaacc ttggaggtaa aaaaattcat aattagtaac aatgtcctaa
2101 atggctattg ttattgtttt aaatagcaat agcattgatt ctataatttc tccatcaaat
2161 tgtaaccgta tatctaat tgtctaggta aagaattaga aatgattata atgagaggga
2221 aatggcaacc cactccagtg ttttttgcctg gagaatccca gggacggggg agcctggtgg
2281 gctgctgtct atgggtcac acagagttgg acacgactga agcgacttag caacagcagc
2341 agcataatga gaggagcagt tggatattca atgcgtttca tgtttcttta attttggaat
2401 gcatagaaat tattataaca caaaattatt tcagttctat gtgtcagttg taaaatgaaa
2461 atttatacag atactttaaa atattaaaaa tgagttatag ttagagaaaa tgttttactt
2521 tatgtctta attgatagac tacatatttt caaaaggac tataaatctc ttctaatatc
2581 tcatattatt caagaagata caattatat tttgaaaatc caccactcta ttcaggacat
2641 aatgggaaaa agtataaaat aagatataaa agaaaacatt gattagtgat tttattgtta
2701 gtagttcatt gtgattcatg ttgaaagctt gatagaagtt aagtaattca aatttaattt
2761 caaaatacac cttaattcaa tgatacttgt agctatttat aaatgaagtt aagttatatg
2821 ctggactcaa cctttataaa cctctagtta ctcagtgatc aatgaattta ttttttgacc
2881 agcttcatca ttagaattgt tcaattaatt gtgtgcatgc agaaaatcta caagctcatg
2941 gtttcaatac cagcctaaat acattgcaca ttgtcacaga gttttttgtaa gcctctgaat
3001 ttaatggagt tttatgatca tacccaataa aaggctagtg gctctgccac ttcctctttg
3061 atggaagaaa tttgttaggt gaatgagcag aagtaaaagt aaagacccat gaagagttga
3121 tttctgtatt cattgctcca gcaaaagaca attttatggt accatgttat acgagaattt
```

```
3181 taagagacta ttctctggtc agttctttgc aaagtctaca ttgggtgaaa cctgcaagaa
3241 aactgcagct tccagttgtg tgcgtgtgct cagtcactca gtcatgtctg acacttggca
3301 acctcatgga ctgtagccca ccaaggttaa aactggtcag tcacgccaac ccagaacact
3361 ggatataatt aatgaaggct ctagtccact gtgatgattc atgaactcgt tacttgggaa
3421 aaatgtcaac ccctagtttt agcatactca tcagagaact gcccccaaat gagaacaaat
3481 tattggcata aactttaag aatagcataa atgtgtacat ttgaaatgaa acgaatgtgt
3541 cttgaatcct catacatttt cttaccagtc ccgtctattt tgtctttgat ccaaactcct
3601 aaatgtttgt gcacatgttt tgtggtgaca atgctgggaa acacagcaac aggacttcat
3661 tattctgttc cttcctgtca ttatggaaac cagtcatcga cctatggcgt gatggcaggt
3721 aagaaaaatt gtctttacat gtaagattga gtttggggac gcttggatgc attttctggg
3781 tcgaagggaa tcttgaccag agtgtatcat gaaattcaga tctcctaacc ttagaaattg
3841 ctgctaaatc caccacttac tataatggtc cctgatctgt aacgccttca gagatcataa
3901 tagttatacc tgatcactgc tgttctccac atgcctgaaa tgaactgcta tgcttcttaa
3961 cgcctgtgtt tgctttgtat gatttttatt ctaattctct gttgccaaac tgctaattgt
4021 cacttgctta tgccattggt gggcttgcct ccagtaataa taaggtagct gctagcctta
4081 tgtaactatt taaatttaaa agtaaattaa ctaaaataag gtcagattta aaattcctca
4141 gttgccaaca gtgagcaagt cagcaaaagc tttaaatgac ttcattgccc gcctccatac
4201 caacagggtt aatgattatg aggtacggaa cttaatagtc atcatttccc ttgagatttt
4261 ggctgttcct tcagttcctg aatttaaaat aaaacaggaa agtgcttaat aatcttttgt
4321 ggctaccaaa gcagatagac taacttatag agcatattcc tcatcacagt atttcttttg
4381 gccatttggt ctgtaaagat aaataagaca ttgaaggcta agagagattt gcagcaactt
4441 tagccatagt tgaatccttg gcagccctgt ctgagatgct ctgagtcttg gataagattg
4501 aaatagtata agttacatac ttatttccct ctggataaag aaagcatcac tatatcaaga
4561 taaactatct tgtttgctga cacttaaatg aaagtattgt tagcaacttt cttaagggaa
4621 agaaaatctg acgtaagaga tccactcatc acaaaattta tgacttaatt ttagaccatg
4681 gctatacagt aattttttg tgcacagaaa ttatttagaa atctcaatct tttatattta
4741 tttctgcagc aagaaataat ttcagtgaca ataaactact aatgttctat gtgaaaaata
4801 taaacgtgtg tgtgtgcatg ctcgtgtaat agttgttatc caagtaggta attaaaaaat
4861 caaacataga tttatgccta taaatttgaa attaaattga acaaagaatt tagttcacca
4921 acctttaatt tctaaaaatt tctcaaattt acactaaata aaacattaaa actttaaaat
4981 aatatattct agaacaaatt agcttttcct acattctgtt agagagcatt ctgaataaac
5041 ttatatcctc acctttatga tgaagtgaaa actgatgttc ttaatggtta cctttaaatc
5101 ttaatgtctc tcttcaataa ttaaaaaata aggaaagtca tattttcctt cctctgtgaa
5161 aacggaccgt ttatgattcg tgtacttagc tgttaatcag tatccatggt taatgagagg
5221 atctctcgtt gaagatgaac tactttcatt atagaaatag tagaacaatg tgcatttagc
5281 cactagcggt gccgctcaaa tgctttctgt ggcctccacc acacttggat tacagagaca
5341 agaaatgatg agtttataga catgtgctac tctttcttgg aggagagagt ccttgctgtt
5401 ccttcacagt agttcccagg aacccacatg caacttaagt catctctgca cccagcaagg
5461 ggcagcaatg agtggaggtt agtgctcaga ccaaacactg tgagatgatt tttactacta
5521 cctccctccc accagatcta ggtagaagct gctgagttca cagctggcct gagaaacctg
5581 acttccttcc tgtttccagg gttgcaggta acaagcccag gttcacactg agagtccaca
5641 ggcaactcag gttgtgctgg tccaagtttc ctcagcaggc cctcagcaaa ctttcatctc
5701 cattagaagt taaaaaggag aggtctttgg aaaaaccttt taaaatgatt caaagcccag
5761 gttggtgata ataatgaaaa aaatggatgt cctaagcttt ggaggtattg ctgtagtctt
5821 aaaccaaaat tacatatatt ttgtcgctga agaaaaaatt caccatgtca agcatagaga
5881 ttatatttga atattttga gagggagatc attaaaatgt gatgtgcttt gtaatttgtt
5941 acaatgtcac tattttgaca tatattcagt attagccttt gcatcacggc agatttaatc
6001 tcagagaatc tgaacctttc tgctgtcatc cccagagaag ctacacaaat tgagtcataa
6061 aacacaggga ttcagaatat tcaggaattc acaaaaggtt taaatacac aagagaaacc
6121 tgataatgtc atttgaattt tctgagaagt ctcaggcgtt catcaaatca gccacttcca
6181 cacaatccac agaagcgtct aatcaccaac aacgaaggtt cattgtcaca tactccatat
6241 aaaagtgaag ctgcacaaag agcaatattt caaagggtgt gaattgctt tatttgaata
6301 tggttatttt atccctatac tctgatgctt atatgtagtc tgagcatttc attaaattaa
6361 taactcactg gaaagcaaga gctacagctc atattttaag ctaaggttgg taggaaggat
6421 tctaatcatc agatgaatcc tctgtacctc atagtccagg tgtggggata tcaaagagaa
6481 tgattggtgg ggtgaaatga attagccaca ccaggaacta attacaaacc tcgttcaagt
6541 tagcatctca aagtgttagt ctcttcacat ccaagttgtg atgggtacca tacatagctc
```

```
6601 tatctgagtt gagttgtggc agctttctac caacttagcc tggttttctc cttgatcttc
6661 tcttcagata cattcatagt taaatttctt cttctgtttc ttctctccta agtacttaaa
6721 taattcaaca gcctgcagga tggataatag gaaacaggga attacaaata ctattcaaaa
6781 atctcttcta gataaacacg aaagaaaact aataacaaaa acctttcaaa attctgattt
6841 ctgggtatac aaggtggtgt ctgttctcat ttgtaaagct gggtgaaagt tggaaaacaa
6901 acttaatgag ctgtgtacct tgcccgccgt cctgtgtgaa ctgggctaat cagctacatg
6961 gtaatgattg ctaaacccag caaggttatg tgttttaatg gccacccaag gtgtgcagta
7021 agagtccttg attaaaaatt gatcttaaga ggaaagcaaa atagctgatg ttggaaaatt
7081 attcaaggag atgaatgctc tttttaaatg agatgtgaat aataagaata aaagatgaat
7141 atagctaaaa agtgtctttt ccacctgggc taggacaaga ggtaccagaa atatgtttca
7201 catttacata ggcaaacagt ctactttgga ggccatctct tcattcttaa attgtctttt
7261 ttctatttcc tttttttctt ttttgtttta tttagtttta tttttgcctc acttattctg
7321 gatgtgttga cactaaggga aggagtaatt ctgaccatct tttgcctctg gatcatgaaa
7381 ggcgcctgca gtagcatgga cactgtgtat tattccttaa attatgtagc atctgtctca
7441 acttcacaac tcaaaagcag ctacaggcaa tctgtaaaca aatggccatg gctgtgctcc
7501 aaatcaacct aatttacaga actaggcaga agacctgttt atatgtggat aggatgtagc
7561 aatgcacaaa agagaaaaaa aatcacaatt caaatttatg atttgtttca cattgtcatg
7621 catgaacgta aaaaaagaaa ataaatggaa atatttaaat gaactgtgct gtgcatctct
7681 acagcaaggt gggggtattt tactatatcc ttcttcccct gtttgttctt ttaaagcttc
7741 tagctcacaa cctcagagat gttgtcagtt agcagctgtc tgagccacgt gctgcagaaa
7801 agcagtgtgc cctgtatcat gggaccttga atcaggtgcc cgtaaggcat gctggacctc
7861 agcttcccat cttctgcttt taaagattta atctctgttc ctctccctcc tctgccgtcc
7921 agaagtccat gcagagcagt tcagagaggc tatggtggat taatctgcag ggtgaaaatc
7981 catcttggac tgtaaagaat gtacaaacct ttccaagcta tttaggtgtg cacttgttct
8041 aggcttatag acaagtttgg tttatcagtg ttttggaaaa tattcatgaa acttctgtgg
8101 cacacaactt cctgcatctt ttctctccgt gctcaaaccc cgacttctta atattccagg
8161 ctttagaaaa acctttaaaa ataccttgtc acatatacca taccaatcaa tccccatttt
8221 ctcccaaata caggatcata taatagaaat cagtttgtct gaccatgctt gtgactgtcc
8281 caaatttctg tttaacatta gtttcaggaa aactgtgtcc ctgtggataa ttgtggatac
8341 tttcagttaa tgaaaaataa cgcagcacac atcgtgtttt ccttcctcct ctagatgcca
8401 aacttttgaa catggtattt cttgtgcact ctttatgaac tcatgttcaa atttattttc
8461 taaatgtcca tttctccaga gtatttataa agtatacact agctttaaat ttttccataa
8521 atagagatgg cacacttcca atatttttgt aaatatttat aaaacttttg tttgaaagca
8581 tttgtttaat gtgaccaaat atatttaaga tgcagaatct ttgagtcatc tgatttccct
8641 gagtacagat tacctgaaaa atgaactgat tattgatgtg gcctattgag gtattcacag
8701 ggcttcactt ctagtttcaa ttgtatagtg aattcatctt agcactcaag gaacgttatt
8761 tgttttttata tgaatttttaa attgtggata aaaaaataca cactttttttc tctgaaaata
8821 aaacaaaagt ccttagataa atattaagta aatgttaaca taaaggtgat aaatttttttt
8881 atatattagt attttactta actagtagaa atctaaaact aacattaggc caaaaatgag
8941 ctttgttaaa atgtaacaaa cattaaaaaa attgaatttt gtaataaatt aaaaattgat
9001 aaaattgctt tttaaaattg tatctggtct attcaatgta gcacccacta aagcaaaaag
9061 tggatgatta acaataacaa caaaaaactg gatagttttg atttttgaaa gtaatatgaa
9121 ttgcttttaga cagaaatagt ttcttttgta tgttttttat atccatgaaa cagctatact
9181 tattttatga tattttgctt aatttctcac ttgtatgtat tttgtttcag aaacataata
9241 gtctactgga taggggtaca cttcaaaatt atattttctc atataaataa tatgagccaa
9301 caacttactg acttgcaata ttctttgctc attacatatt gatatattaa tttaagattt
9361 atatattctg gcaaaataca ctattactca tgtctgattt ctgactgtat ttatagagaa
9421 attataaaata gcataaaact gatgtatttt ttagtaagtt tctaagaatg attactgcct
9481 atttctata gtcatttata tttaatttat actcataaga aaaatgatta attattgaat
9541 attttattta tatcaaaatg tcttggttat acccatgtca tttaatataa agtgaaatcc
9601 ttatgaataa aaatgtaata tactgctgaa gaaaacagaa ataaaatgtg tgggaatttg
9661 gcttatacca tcctgtcacc aatactccct gactgagatt ctctcttctt tccaaatgaa
9721 gaatgaaatc tagaagcaat taaacaatta aatcatgtag ttttttgaga tttctcattt
9781 aactaactca atggattcag tgcttcatca tttatgaggg attatgtatt gtatctcaga
9841 gaaggaaatg gcaactccag tattcttgcc tggagaatcc cagggacaga ggagcctgtt
9901 gggctgctgt ccatgggggtc gcacagagtc ggacacgact gaagcgactt agcagcagca
9961 gcagcagcat gtatcatatc tagaattgca cccttccttg acacttaact ttttcttctt
```

```
10021 aaatagtaat caagaaatga ttccatcata gtatattttg caagaatctt gttgctgacc
10081 ttctaataga tctttaaaag ttacttttg tcgacatcca tcattaccat taaatctatt
10141 taaaccttat taatgtattt tttgttctca taattttcgt tttacttgcc tttactaaat
10201 taagcattta ctgataaaac attggatttc ttaatgctgt aaaatcaatt tttcaatgct
10261 atgaaaattt cccagaatag cacttaacat acaccttgat tataattaag aaaatataca
10321 ttctggtaga gttgaacctc agattcacaa taacaaatga aaagattttt gtttgttttt
10381 ggggagccat gctgaattcc ataaccagga atcaaaccca tgccctctat actggaagga
10441 tgaagtctta accactggac tgctatggaa gtcttttaag agaaaaacaa tgatggaaaa
10501 ctcacacttt tttgaaattt gcttatttct atttaaatta tttgcaagtc cctggttctt
10561 tcctttggct ttgcattatc tttgtttcca ctgctcccag gaaggtggaa aaaaaagatc
10621 ctatttatac taagctacac tgacttctac ttcagaaaag caaatgtcag gtaaccttt
10681 agaactgaga ctggctgtca cagaacaatc tgatgggcca aaattttcca tgtatcaaaa
10741 tgagggataa ttacaaatgg tccttttctt gttgttacag ggagcttaac ccattgtctt
10801 tataagtttc ctgaccacac gttgagtcat ggttttcctc ccatgcatca gcctctcctt
10861 tcagaggacc ccactgccgc tgatttcaag caggagctca ggcggaaaag caaattggtt
10921 gaagagccaa tagacatgga ttctccagaa atccgagaac ttgaaaagtt tgccaatgag
10981 tttaaagtga gaagaattaa gctaggtagg tgcttgttaa cagctgtggg acacacaact
11041 ccgtctgcaa agtcttactc tattactgtt taatctctta catgctgctc agaagtctaa
11101 gacagttctc attctacatc tctactgtgg atgtaagttg aattatgaaa acctatagca
11161 accttcattt ccttgtaaat tcttagcagc aaaaatatat agatttctaa attaatggtc
11221 tccttttcaa acataagttt agaaatacct ttgttttatt tgaattaata cctttgtgtg
11281 attcaaaagc taaaagctg tgagaattgt atccctctgc ttatccttcc tgtttatcag
11341 tgttattagt ttctgtgaat ccttctattc tatgcatatt catataagca aattcatgta
11401 tttcttcata tagacatttt tcatttgact attttggaga gctttcagta ttagttttt
11461 agagagctct tcttttaat gcatctctca attccatttt atgaatatat taccagtctc
11521 ctactgatgg aatttagatg gtcttcaatc ttatgttact gaagacaatg atgcaatgat
11581 taacttcata aatagcattt tgcaccgata aaaatatatg tgcagggaaa gtgttaaaag
11641 caaaattgtt tgattgaaga gcatgtgtat ttgtaatttc agtagatgtc aaattggtct
11701 ctatgtaaat tctaacaaat cttattgcca ccatgagtat ctccttttgcc actcttcaga
11761 atatgaattc tgttaaggca gaagtttttt gtttttttgtt tatttccttt gctttctcct
11821 taatggcata tcctcagcac ttggaacagt gactggcatg tagaataaaa aatagttatt
11881 gaagggaaaa gatgctatta atcttttgga cctttgcaaa tcagttaggt gaaagtagca
11941 gtttcatttt aaatttccct tatgagtgaa gagtgaaaga agttttcat gtgttggaca
12001 gtcatttgta attccttttc tgtgagcgat ctgttcatag cctttgctca ctttctaggg
12061 tgaagtgttt ttaatgtaaa taatcataat aattaaccct gatttaaatg catgaaatat
12121 attttaatg gattgaactg atagtacaaa cttctgcatt tgtggactga gccattggta
12181 acttttaatg atatcaattg atgggcatca tatgtaatca ttttatgcat acaggtatat
12241 agccttgggc cctgaattaa tatgtagtta ctgtttgtca taaacacagc agtaggcatc
12301 tttatgacat tcattttcaa tttactttt atatgactgt gaatgtttca aattctacat
12361 tgatgacatt tgtcaactta tattctgaga atgtttgaga caatctatga aaacttttg
12421 cctggagata gaagcattac caaatgatat aataaatgct tggtgatata cataaaatgt
12481 tgtgtgacca aagtctcata ataagcatgc ttttagggaa agtaaacaca gttcttagtt
12541 ttatttgtta acttcaacat gttgaatttt tcactcttac agctgagata aaaatatttg
12601 tgatatatca ccatatagtt tacatattat attttaatat ctatagattt tgagcatatt
12661 tcaacagatg cctaataata atgattagag agaattttta aatgtcttct aaagtgtgta
12721 ttaaggattc cctggtagaa cagctggtaa agaatccacc tgcaatgcag gacaccccag
12781 ttcaattcct gggtcaggaa gatcagttgg agaagggata ggctacccat tccagtattc
12841 ttcggcttcc cagtggctca gctgttaaag aatctgcctg ctatgaggga gatctggatt
12901 cagtccctgg gttgggaaga tcccctggag atgggaacag ctacccactc cagtattctg
12961 gcctggagaa ttccatgtac tgtatagtcc atggggttgc aaagaatagt ctgactacac
13021 ttatattagg ttataaaaat gattcatgta taattactac agtatatagc acagtggcaa
13081 aaaaataaat ctggatacat taaaaagaat catttcacta ctttatacct atgctacatt
13141 gtctagaaac ttttcttata tattttgca agtgtgttt aacacattta tccagtttgg
13201 ctaaatatga atggcagatg ttcctatctg aattcttttg gcttctaaaa tattaactta
13261 ttaactagaa ggattttttt aaaatactag acaattctac actgcataac cttactgtta
13321 ttctaaattg ctaacaaatt tatcgttaaa agcaatattt aatagttgac aaaaatacta
13381 cacaaattta tacaatagtg gacccaaatc agtgttctct gcaaaactga agctcatggc
```

```
13441 ctttgttatt ctttcacagg atacacccag acaaatgttg gggaagctct ggcagctgtg
13501 catggctctg aattcagtca aacaactatc tgccgatttg aaaacctgca gctcagcttc
13561 aaaaatgcat gcaaactaaa agcaatatta tccaaatggc tggaggaagc cgagcaagta
13621 ggaggtacaa aagctgtgtt tctggaaaca gtgatgtttt aacctaaaaa caatggtttc
13681 cctcagttga atttgtacta aagcaagagg tttgaagttt ggtttgattt ttctctttga
13741 catgaaaaat aagtatcttg tttcatcaca ctatgaagaa aagcaaggcc agtgaaagtg
13801 tagaaataaa tttattgaga aggtaaataa tgagagaata aatatatag ggaaagtttc
13861 tacacaatgt ggcataggtg tgaagtggtg aaatgattct ttttaatgta tccagatttt
13921 ttcctgctgt gctatatact gtagtaatta ttcatgaatc atttttacaa cctaatataa
13981 gtgtagccag agcattcgca cacaccgttc tttctagtga atagcaagca attgctagat
14041 aaacaattta atgtgataaa aattatctac ttatattaat gtcaaggctg gctaaagagc
14101 aagatttgat agcatttaga gcaactgttt caacaaagat agggtatgat ttaaagacaa
14161 ctgttaatat ttataaagtt aatattttt tctgtgttaa cattttaatc tagggcttgt
14221 aatctaaaat gatgtatact gcaaatattt aaaacaaaaa tgtatggtaa ttctattttg
14281 tattgtttta taaagaaact ttaaatccaa atctgatagt taaaaaaaaa acctggtttg
14341 tttttgtaat tattcattgt tttcgcatca cagctttata caatgagaaa gttggtgcaa
14401 atgaaagaaa aaggaaacgg agaacaacaa tcaggtatac ttttgagata ttaagagtta
14461 gtggagaaga aaatgatatt ttacaaatgg aatgaacatt tgagtataat atagtttcaa
14521 tataacataa aaatgaatag agccaattga gaaaataggt gaaaaagcac aacattcaat
14581 aaattacttc tgagaaacag ctggaaattt aaaatttgat ggaaaaatat gtattgtttg
14641 attcaagaac agttttgctc tgcaagtttt ggataaaaca gaagctgtac aatcacagct
14701 aaaaagaatg actgtttcta ctgtgtcata atgtgttgat ttatgtttag acataaatct
14761 tgctccggga aagaccccat ggactgtagc ctacaggttc ctctgtccat gggatttcc
14821 aggcaagaat aatggagtgg gttgccattt ccttctccag gagatcttcc cgacccaggg
14881 attgaacccg gatctcctac attgtaggca gatgctttac catctgagcc acaagggaag
14941 tcatctatct atattatttc aaattaacaa aactggtcac tagtatttta gttgcttaaa
15001 gttcaaaatg acttctagca tttcaagcca gattgttcat ttatctttt gtagtttccg
15061 tgaggctcat ggaggaattg ctaatataca ggttttgttt tggttggtta gttgtacact
15121 aaacatttca ataacctgag ttctggggga catttagaaa tgcatacaga attattttct
15181 tctcagtaag tcagtgccct cttgtggcag aaagtggata aacaatgtcg gggttccctc
15241 cttaatttct tcctgtgact ctggtaaaag gagcctacat gagacaagca tctaaatgtt
15301 caaaaaaact tcacatttat tattgttgaa aagctttgaa ggtgttttca gtgtctttag
15361 gtttccttt tacgttaatg ttagtactaa tatttaggaa atgtaaccta acttgatttt
15421 gatgggccta aaccatcatc tcccttcttt cctgccaact cctcacctcc cagtattgct
15481 gctaaagacg ccctggagag acactttgga gaacagaata agccttcctc tcaggagatc
15541 ctgcggatgg ctgaagaact aaacctggag aaagaagtgg tgagggtttg gttttgtaac
15601 cgaaggcaga gagaaaaacg ggtgaagaca agcctgaatc agagtttatt tactatttct
15661 aaggagcatc tcgaatgcag ataggctctc ctattgtgta atagcgagtg tttctacttt
15721 tcattccttt ctcttctcca gccaaaatag aaattagtta tttggttagc ttcaaaaaat
15781 cacatcagta attttgcag aagtgtttct tttctacttt aaaaataaat acaatttaaa
15841 ttatgttgat gaattattct cagaaggcac attgtacatt ttaagccaaa gactaatagg
15901 attcaaacaa tgattctgtc cctttcacta tatctttccc tctatctctc cc
```

METHODS AND COMPOSITIONS FOR IMPROVED CATTLE LONGEVITY AND MILK PRODUCTION

GOVERNMENT INTEREST

This invention was made with United States government support awarded by the following agencies: USDA/CSREES 05-CRHF-0-6055. The United States government has certain rights in this invention.

CROSS-REFERENCE TO RELATED APPLICATION

60/986,241
Filed Date: Nov. 7, 2007

FIELD OF THE INVENTION

The present invention relates to a method of cattle progeny testing using molecular genetic methods by assaying for the presence of at least one genetic marker which is indicative of longevity and improved milk production.

BACKGROUND OF THE INVENTION

Dairy cows are significant investments for dairy farmers, and enormous efforts, such as animal breeding and artificial insemination, have been and continue to be invested in ensuring that the animals have high and sustained productivity, and that the milk produced are of high quality. Traditional breeding techniques involve the studying of sire progenies, and evaluating their traits including milk production ratings (transmitting abilities) to guide further breeding. This standard technique is time consuming and costly, requiring years to evaluate the true genetic value by progeny testing each bull. Many cows must be bred and give birth to offspring. The females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of the environmental and developmental variants. There is thus a need for a method of genetically evaluating cattle to enable breeders to more accurately select animals at both the phenotypic and the genetic level.

Marker-assisted selection can lower the high cost of progeny testing currently used to improve sires, since young bull progeny could be evaluated immediately after birth, and young bulls that are determined by genetic testing to have undesirable markers would never be progeny tested. Testing may even be conducted prior to birth, for the presence/absence of the marker. Therefore, there is also a need for genetic markers for improved milk production traits.

POU1F1 is a member of the tissue specific POU (Pit, Oct, Unc) homeobox transcription factor DNA binding protein family that is found in all mammals studied so far (Bastos et al., 2006; Ingraham et al., 1988; Ingraham et al., 1990). The pituitary specific expression of POU1F1 is required for the activation of growth hormone (GH), prolactin (PRL), and thyroid stimulating hormone (TSH) (Li et al., 1990). These genes are involved in a variety of signaling pathways that are important for many developmental and physiological processes, including pituitary gland development (Li et al., 1990; Mullis, 2007), mammary gland development and growth (Svennersten-Sjaunja and Olsson, 2005), milk protein expression (Akers, 2006), and milk production and secretion (Svennersten-Sjaunja and Olsson, 2005). Moreover, binding of GH and PRL to their receptors on the cell membrane triggers a cascade of signaling events including the JAK/STAT pathway, which has been shown to be required for adult mammary gland development and lactogenesis (Liu et al., 1997).

Mutations in POU1F1 often result in severe GH deficiency as well as defects in development (Mullis, 2007). In a dwarf mouse model, mutations in POU1F1 lead to the loss of three pituitary cell types—somatotropes, lactotropes and thyrotropes—(Li et al., 1990). Lactotropes produce prolactin, which is necessary for mammary gland development and lactation.

Several genes in the same pathway of POU1F1 have been reported to be associated with different milk production and health traits. For example, growth hormone receptor (GHR) and prolactin receptor (PRLR) have shown associations with milk yield and composition (Viitala et al., 2006). Also, the signal transducer and activator of transcription 1 (STAT1) and osteopontin (OPN) genes have been shown to have significant effects on milk yield and milk protein and fat yields in Holstein dairy cattle (Cobanoglu et al., 2006; Leonard et al., 2005; Schnabel et al., 2005). The uterine milk protein (UTMP) is another gene in the pathway of POU1F1 that has been found to be associated with productive life in dairy cattle (Khatib et al., 2007b).

POU1F1 is located on bovine chromosome region BTA1q21-22 (Woollard et al., 2000), where multiple quantitative trait loci (QTL) affecting milk production traits have been identified (Georges et al., 1995; Nadesalingam et al., 2001). In previous studies, POU1F1 variants have been reported to be associated with milk yield and conformation traits (Renaville et al., 1997; Tuggle and Freeman, 1994). Taken together, the biological functions of POU1F1 and associations with production traits of genes in the same pathway of POU1F1 suggest that this gene could be functionally involved in milk yield and composition traits.

SUMMARY OF THE INVENTION

The present inventors investigated the effects of POU1F1 on health and milk composition traits in two independent North American Holstein cattle populations. A pooled DNA sequencing approach was used to identify single nucleotide polymorphisms (SNP) in the gene. A SNP (C/A) in exon 3 of POU1F1 that changes a proline to a histidine was identified. A total of 2141 individuals from two independent North American Holstein cattle populations were genotyped for this SNP using a modified PCR-RFLP method. The frequencies of allele A were 14.9% and 16.8% in the two examined populations respectively. Statistical analysis revealed significant association of POU1F1 variants with milk yield and productive life, which makes POU1F1 a strong candidate for marker assisted selection in dairy cattle breeding programs.

Based on the results, the present invention provides an isolated nucleic acid molecule comprising a polymorphic site of position 10793 ("SNP 10793") of SEQ ID NO: 1 and at least 17 contiguous nucleotides or bases of SEQ ID NO: 1 adjacent to the polymorphic site, wherein the nucleic acid molecule comprises an adenine base at position 10793 of SEQ ID NO: 1. It is recognized that SEQ ID NO: 1 is already known, and the nucleic acid molecule therefore does not encompass one that consists of SEQ ID NO: 1.

Preferably, the nucleic acid molecule which comprises at least 15, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting single nucleotide polymorphism (SNP) in bovine POU1F1 gene, wherein the POU1F1 gene has a nucleic acid sequence of SEQ ID NO: 1, the method comprising determining the identity of a nucleotide at position 10793, and comparing the identity to the nucleotide identity at a corresponding position of SEQ ID NO: 1.

In another embodiment, the present invention provides a method for genotyping a bovine cell, using the method above. Suitable bovine cell may be an adult cell, an embryo cell, a sperm, an egg, a fertilized egg, or a zygote. The identity of the nucleotide may be determined by sequencing the POU1F1 gene, or a relevant fragment thereof, isolated from the cell. The POU1F1 gene or a relevant fragment thereof is isolated from the cell via amplification by the polymerase chain reaction (PCR) of genomic DNA of the cell, or by RT-PCR of the mRNA of the cell. Preferably, the PCR or RT-PCR is conducted with a pair of primers having the following sequences:

```
                                          (SEQ ID NO: 2)
CAAATGGTCCTTTTCTTGTTGTTACAGGGAGCTTAAGGC (SEQ ID NO: 3)
CTTTAAACTCATTGGCAAACTTTTC.
```

In a further embodiment, the present invention provides a method for progeny testing of cattle, the method comprising collecting a nucleic acid sample from the progeny, and genotyping said nucleic sample as described above.

Further provided is a method for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, genotyping the developing embryo, and terminating pregnancy if the developing embryo does not have adenine (A) at position 10793. Preferably, pregnancy is terminated if the embryo is homozygously A at position 10793.

In a preferred embodiment, the method is used for selectively breeding dairy cattles, comprising selecting a bull that is hemizygously or homozygously A at position 10793 of its POU1F1 gene, and using its semen for fertilizing a female animal. Preferably the bull is homozygously A at position 10793. More preferably, the female animal is also hemizygously or homozygously A at position 107931, preferably homozygously A. MOET procedure may be preferably used for the selective breeding.

The present invention also provides a method for testing a dairy cattle for longevity or its milk production trait, or both, comprising genotyping its cells, wherein a cattle being homozygously A at position 107931 indicates that the cattle has desirable longevity or milk production trait.

DESCRIPTION OF THE DRAWINGS

FIG. 1 shows the POU1F1 gene sequence (SEQ ID NO: 1) where the relevant polymorphic site is shown.

DETAILED DESCRIPTION OF THE INVENTION

Figure 2:
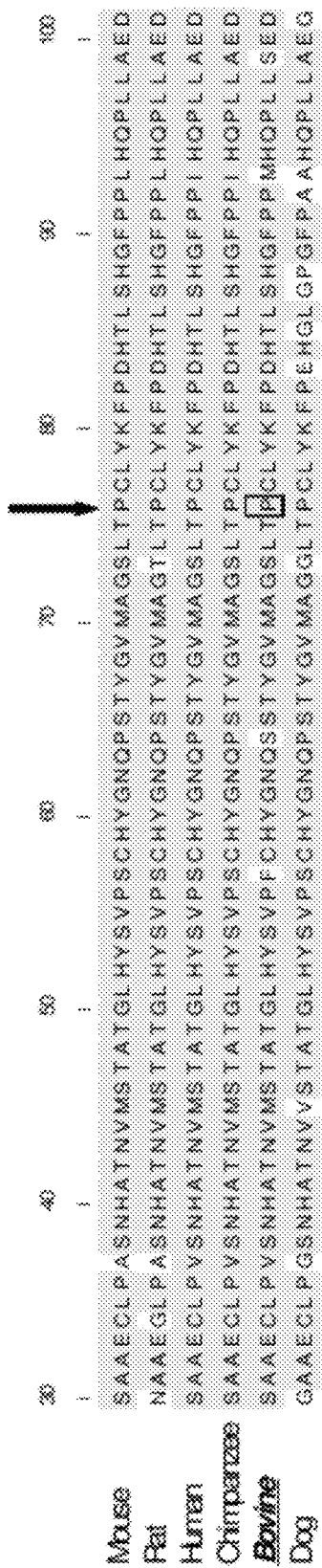
FIG. 2 shows the protein sequence alignment of POU1F1 from mammalian species. Protein sequences of POU1F1 from mouse (SEQ ID NO. 4), rat (SEQ ID NO. 5), human (SEQ ID NO. 6), chimpanzee (SEQ ID NO. 7), bovine (SEQ ID NO. 8), and dog (SEQ ID NO. 9) were aligned using the multiple alignment algorithm ClustalW and visualized with Jalview (EBI). Numbers on the top are the relative positions of amino acids. The position of the Pro76H is mutation is indicated by the arrow.

It has been found that a specific site, i.e. position 10793 (see FIG. 1), in the POU1F1 gene sequence is polymorphic. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may result in functional differences, through changes in the encoded polypeptide, changes in mRNA stability, binding of transcriptional and translation factors to the DNA or RNA, and the like. Polymorphisms are often used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, SNPs are used for determining the genotypes of the POU1F1 gene, which are found to have strong correlation to longevity and milk production traits.

In the context of the present specification, the provided sequences also encompass the complementary sequence, including those corresponding to the provided polymorphisms. In order to provide an unambiguous identification of the specific polymorphic site the numbering of the original POU1F1 sequence in the GenBank is shown in FIG. 1 and is used.

The present invention provides nucleic acid based genetic markers for identifying bovine animals with superior longevity and milk production traits. In general, for use as markers, nucleic acid fragments, preferably DNA fragments, will be of at least 12 nucleotides (nt), preferably at least 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or C. An oligonucleotide probe can be used for such purpose. Preferably, the oligonucleotide probe will have a detectable label, and contains an A at the corresponding position. Experimental conditions can be chosen such that if the sample DNA contains an A at the polymorphic site, a hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the POU1F1 gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 10793 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl.

Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should be at the center of the probe fragment used, whereby a mismatch has a maximum effect destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the POU1F1 gene of the sample of interest may be amplified via PCR and directly sequenced, and the sequence be compared to the wild type sequence shown in FIG. 1. It is readily recognized that, other than those disclosed specifically herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved milk production traits.

Further provided is a method for genotyping the bovine POU1F1 gene, comprising determining for the two copies of the POU1F1 gene present the identity of the nucleotide pair at position 10793.

One embodiment of a genotyping method of the invention involves examining both copies of the POU1F1 gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

The present invention discloses the association between POU1F1 and milk production and longevity in a total of 2141 individuals from two independent Holstein dairy cattle populations. SNP10793 allele A was associated with a significant increase in PTA for milk yield in the CDDR granddaughter design population but not in the daughter design UW resource population. Although the granddaughter design has more power than the daughter design for detecting QTL (Weller et al., 1990), the use of PTA values in the CDDR population may limit the detection of epistasis and dominance effects. Thus, to test whether there is any genetic interaction between the A and C alleles of SNP10793, genotypic effects were estimated in the UW data. Genotype AA was found to be associated with an increase in milk yield and productive life compared to the CC and AC genotypes. This is an indication for complete dominance of the C allele over the A allele in determining the phenotypic value of productive life and milk yield. Also, this could explain the lack of significant association between POU1F1 and productive life when PTAs were used in the allele substitution model.

A different SNP located in exon 6 of POU1F1 has been reported to be associated with milk yield (Tuggle and Freeman, 1994; Renaville et al., 1997). The population size used in those studies was relatively small (115 and 98, respectively) compared to a total of 2141 individuals from two independent populations investigated in the current study. In addition, the SNP reported in the current study is a missense mutation compared to a synonymous mutation SNP reported in Tuggle and Freeman (1994) and Renaville et al. (1997).

The candidate gene approach has been widely and successfully used in medical and agricultural studies to identify underlying genes responsible for complex traits such as susceptibility to diseases and production traits. We have used this approach and identified a number of genes including OLR1 (Khatib et al., 2006, Khatib et al., 2007a), PI (Khatib et al., 2005), OPN (Leonard et al., 2005), STAT1 (Cobanoglu et al., 2006), and UTMP (Khatib et al., 2007b) that are associated with milk production and health traits. In addition to the functional candidate gene approach, positional information about the investigated gene is usually incorporated into this approach to identify candidate genes. However, production traits are very complex by nature and determined by multiple factors including single gene effects, interaction between genes, and environmental factors. Therefore, in addition to positional and functional information of the single gene, functional information of the signaling pathway and regulatory network in which the candidate gene is involved should be incorporated to aid the identification of candidate genes. In light of this notion, POU1F1 was chosen as a candidate gene for milk production traits. First, POU1F1 is a transcription factor that controls the expression of GH and PRL, two important genes in mammary gland development and milk production and secretion. Second, genes that are downstream of the POU1F1 signaling pathway (e.g. STAT1, OPN, UTMP) have been reported to be associated milk production and health traits. Third, the amino acid proline is highly conserved among mammalian species; as such mutations at this position could change the function of the protein.

In summary, based on the positional, functional, and regulatory information, POU1F1 was chosen as a candidate gene for investigation of association with milk production and health traits. We identified SNP10793, a C to A nucleotide change that changes a proline to a histidine in the protein. The rarer AA genotype was associated with a significant increase in productive life and milk yield. These results suggest that POU1F1 could be used in marker assisted selection programs in dairy cattle.

The following examples are intended to illustrate preferred embodiments of the invention and should not be interpreted to limit the scope of the invention as defined in the claims.

EXAMPLES

Materials and Methods

Cattle Population and Phenotypic Data

Semen samples from 31 Holstein sires and their 1299 sons were obtained from the Cooperative Dairy DNA Repository (CDDR) of the USDA Bovine Functional Genomics Laboratory (Beltsville, Md.). Blood samples (n=842) were obtained from the University of Wisconsin (UW) resource population (Gonda et al., 2006; Cobanoglu et al., 2006; Khatib et al., 2007b). Phenotypic data including predicted transmitting abilities (PTAs) and yield deviations (YDs) for milk yield, fat yield, protein yield, productive life, and SCS score were obtained from the USDA Animal Improvement Program Laboratory (Beltsville, Md.).

Single Nucleotide Polymorphism (SNP) Identification

SNP were identified in POU1F1 using the pooled DNA sequencing approach as described in Leonard et al. (2005). Briefly, genomic DNA was extracted form 30 individuals, quantified using a spectrophotometer, then equal amounts of DNA from each individual were pooled together and subjected to PCR amplification using different pairs of primers designed in POU1F1. PCR products were sequenced using forward and reverse primers and SNP were identified by visual inspection of the chromatograms. To validate SNP identified in the pools, individuals composing these pools were also sequenced.

SNP Genotyping

Genotyping of the identified SNP was done by a PCR-restriction fragment length polymorphism (PCR-RFLP) based method. To genotype SNP3699, primers (forward: atactcatcagagaactgcc (SEQ ID NO: 10) and reverse: cattaac-cctgttggtatgg (SEQ ID NO: 11)) were used to amplify a 771 by genomic fragment of POU1F1. The PCR products were digested with the restriction enzyme TaqI. Depending on the availability of restriction enzymes and suitability of the sequence, a PCR primer can be designed to change the nucleotide sequence near the SNP to create a restriction site. For SNP10793, primers (forward: caaatggtccttttcttgttgttacagg-gagcttaaggc (SEQ ID NO: 2) and reverse: ctttaaactcattg-gcaaacttttc (SEQ ID NO: 3)) were designed to amplify a PCR product of 234 bp. Two Cs were mutated to Gs at positions 2 and 3 nucleotides upstream of the SNP in order to create a recognition site for the restriction enzyme StuI.

A touchdown PCR program was used as follows: initial denaturing at 94° C. for 5 min, followed by 33 cycles of 94° C. for 45 s, touchdown annealing for 45 s (from 63° C. to 50° C., stay at 50° C. for 25 cycles), and 72° C. for 45 s, and final extension at 72° C. for 7 min. The PCR products were subjected to TaqI or StuI (Promega, Madison, Wis.) digestion according to manufacturer's instructions, followed by 2% agarose gel electrophoresis. The A allele of SNP3699 was indicted by two bands of 338 and 433 bp, and the G allele was indicated by three bands of 84, 254, and 433 bp. For SNP10793, the C allele was indicated by two bands of 38 and 198 bp, while the A allele was indicted by a single band of 234 bp.

Statistical Analysis

For the CDDR population, association analysis between number of alleles at the POU1F1 locus and productive traits was carried out through a weighted least square allele substitution model of the following form:

$$y_{ij} = \mu + sire_i + \beta x_{ij} + \epsilon_{ij}$$

where $y_{ij}$ is the PTAs of the trait considered, $\mu$ represents a general constant, $sire_i$ is the fixed effect of the $i^{th}$ sire, $\beta$ represents half of the allele substitution effect ($\alpha/2$), $x_{ij}$ is the number of A alleles (0, 1, 2) at SNP3699 or SNP10793, and $\epsilon_{ij}$ is the residual term.

For the UW resource population, association of POU1F1 polymorphism with production traits was evaluated with the following mixed effect model:

$$y_{ijklm} = \mu + h_i + s_j + mgs_k + d_{ijkl}\tau + p_m + \epsilon_{ijklm}$$

where $y_{ijklm}$ represents in turn the yield deviation for milk protein and fat or productive life of daughter l of sire j and maternal grandsire k; $\tau$ represents an effect associated with *M. Paratubercolosis* infectious status; $d_{ijkl}$ is an indicator variable assuming values 0 or 1 for non infected and infected cows respectively; $p_m$ represents the effect of POU1F1 (1=AA, AG, GG). Herd h, sire s and maternal grand sire mgs effects were fitted in the model as random. In the analysis, correlation between individuals was not accounted for and therefore variance structure for sire and maternal grand sire effect had form, $I\widehat{\otimes}\sigma_s^2$ and $I\widehat{\otimes}\sigma_{mgs}^2$ respectively. Variance structure for herd effect was $I\widehat{\otimes}^2{}_h$. Standard assumptions were made for the residual term $\epsilon_{ijklm}$. Additive genetic effect was estimated as half of the difference between the two homozygotes groups and dominant genetic effect was computed as the difference between heterozygote and the average of two homozygotes. Degree of dominance was estimated as the ratio of dominant effect over additive effect (Falconer and Mackay, 1996) with values approaching 1 indicating complete dominance (same effect for heterozygote and homozygote). All statistical analyses procedures were implemented using "lm" and "lme" of the freely and publicly available R software v. 2.5.1.

Example 1

Identification of SNP

Sequencing of 30 grandsires from the CDDR populations and of the pooled DNA samples revealed four SNP identified in protein coding exons of POU1F1. An A/G SNP at position 3699 (GenBank accession number NW_001501776) was identified in exon 2, and 3 SNP were identified in exon 3: SNP A/C at position 10793, SNP C/T at position 10822, and SNP A/G at position 10863. Importantly, SNP3699 (exon 2), SNP10822 (exon 3), and SNP10863 (exon 3) were found to be in complete linkage disequilibrium (LD), therefore only SNP3699 was used for genotyping. SNP10793 (exon 3) was not in LD with other SNPs, therefore it was genotyped independently. SNP3699, SNP10822, and SNP10863 are synonymous mutations whereas SNP10793 is a missense mutation in which the change from a C to an A (minor allele) changes amino acid 76 of the POU1F1 protein from proline (Pro) to histidine (His). Alignment of protein sequences of POU1F1 from mouse, rat, human, chimpanzee, bovine, and dog using the multiple alignment algorithm ClustalW, revealed that proline is highly conserved among these species (FIG. 2).

Example 2

Association of POU1F1 with Milk Production and Health Traits

The allele and genotype frequencies of SNP3699 and SNP10793 and the corresponding chi square test of Hardy-Weinberg equilibrium (HWE) are listed in Table 1. The genotype frequencies were consistent with those expected of a population in Hardy-Weinberg equilibrium. Association testing of SNP3699 in the CDDR population did not show significance with any of the examined traits (data not shown), so this SNP was not investigated in the UW resource population.

In contrast to SNP3699, SNP10793 was found to be significantly associated (P=0.027) with milk yield in the CDDR population using the allele substitution model (Table 2). PTAs analysis in the UW population did not detect association of milk yield with POU1F1 locus. However, in the YD analysis, AA genotype was found to be associated with higher milk yield (Table 3). The AA genotype was also found to be positively associated with productive life. Because of PTAs additivity assumptions, dominance effects were estimated in the UW population using yield deviation data (Table 3). For both, yield and productive life, the ratio of dominant effect over additive was close to 1, suggesting complete dominance. Frequencies of the allele A of SNP10793 were 15% and 17% in the CDDR and UW populations, respectively (Table 1).

TABLE 1

Allele and genotype frequencies and tests HWE of the identified SNPs of POU1F1 in the CDDR and UW resource Holstein cattle populations

| Population | | MAF[a] | Genotype | X²(DF = 1)[b] |
|---|---|---|---|---|
| CDDR | SNP3699 (n = 480)[c] | 0.18 | n(AA) = 12, n(AG) = 149, n(GG) = 319 | 1.228 |
| | SNP10793 (n = 1299) | 0.15 | n(AA) = 31, n(AC) = 325, n(CC) = 943 | 0.227 |
| UW | SNP10793 (n = 842) | 0.17 | n(AA) = 26, n(AC) = 231, n(CC) = 585 | 0.300 |

[a]MAF: minor allele frequency, A allele in SNP3699 and A allele in SNP10793.
[b]For degree of freedom of 1, the 5% significance level for X² is 3.84.
[c]n = number of individuals genotyped

TABLE 2

Estimates of the allele substitution effects and standard errors (SE) of SNP10793[a] for production trait PTA values in the CDDR and UW Holstein cattle populations

| Traits | CDDR α/2 ± SE | UW α/2 ± SE |
|---|---|---|
| Milk yield | 72.24 ± 32.64* | 37.11 ± 35.02 |
| Fat yield | 1.69 ± 1.23 | 1.59 ± 1.34 |
| Fat percentage | −0.362 ± 0.500 | 0.052 ± 0.482 |
| Protein yield | 1.22 ± 0.835 | 0.792 ± 0.936 |
| Protein percentage | −0.353 ± 0.229 | −0.101 ± 0.231 |
| Productive life | −0.520 ± 0.684 | 0.028 ± 0.047 |

[a]The effect of substituting allele C with allele A.
*P < 0.05.

TABLE 3

Estimates of the genotypic effects, standard errors (SE), and additive and dominance effects of SNP10793 in the UW resource Holstein cattle population

| Effect | Milk yield | P value | Productive life | P value |
|---|---|---|---|---|
| Genotype effect[a] | | | | |
| AC | −13.26 ± 150.88 | 0.9301 | 0.46 ± 0.87 | 0.5973 |
| AA | 722.55 ± 378.80 | 0.0592 | 5.17 ± 2.25 | 0.0240 |
| Dominance effect[a] | −374.54 ± 220.66 | 0.0926 | −2.12 ± 1.30 | 0.1065 |
| Additive effect | 361.28 ± 189.40 | 0.0592 | 2.58 ± 1.12 | 0.0240 |
| Degree of dominance[b] | 1.04 | | 0.82 | |

[a]Estimates of yield deviations from the UW population, the effect of genotype CC was arbitrarily set to zero
[b]Degree of dominance was estimated as the ratio of dominance effect over additive effect

REFERENCES

Akers, R. M. 2006. Major advances associated with hormone and growth factor regulation of mammary growth and lactation in dairy cows. J. Dairy Sci. 89(4):1222-1234.

Bastos, E., I. Santos, I. Parmentier, J. L. Castrillo, A. Cravador, H. Guedes-Pinto, and R. Renaville. 2006. Ovis aries POU1F1 gene: cloning, characterization and polymorphism analysis. Genetica 126(3):303-314.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89(11):4433-4437.

Falconer, D. S. and T. F. C. Mackay. 1996. Introduction to Quantitative Genetics. 4th ed. Addison Wesley Longman Limited, England.

Georges, M., D. Nielsen, M. Mackinnon, A. Mishra, R. Okimoto, A. T. Pasquino, L. S. Sargeant, A. Sorensen, M. R. Steele, X. Zhao, and et al. 1995. Mapping quantitative trait loci controlling milk production in dairy cattle by exploiting progeny testing. Genetics 139(2):907-920.

Gonda, M. G., Y. M. Chang, G. E. Shook, M. T. Collins, and B. W. Kirkpatrick. 2006. Genetic variation of *Mycobacterium avium* ssp. paratuberculosis infection in US Holsteins. J. Dairy Sci 89(5):1804-1812.

Ingraham, H. A., R. P. Chen, H. J. Mangalam, H. P. Elsholtz, S. E. Flynn, C. R. Lin, D. M. Simmons, L. Swanson, and M. G. Rosenfeld. 1988. A tissue-specific transcription factor containing a homeodomain specifies a pituitary phenotype. Cell 55(3):519-529.

Ingraham, H. A., S. E. Flynn, J. W. Voss, V. R. Albert, M. S. Kapiloff, L. Wilson, and M. G. Rosenfeld. 1990. The POU-specific domain of Pit-1 is essential for sequence-specific, high affinity DNA binding and DNA-dependent Pit-1-Pit-1 interactions. Cell 61(6):1021-1033.

Khatib, H., E. Heifetz, and J. C. Dekkers. 2005. Association of the protease inhibitor gene with production traits in Holstein dairy cattle. J. Dairy Sci 88(3):1208-1213.

Khatib, H., S. D. Leonard, V. Schutzkus, W. Luo, and Y. M. Chang. 2006. Association of the OLR1 gene with milk composition in Holstein dairy cattle. J. Dairy Sci. 89(5):1753-1760.

Khatib, H., G. J. Rosa, K. Weigel, F. Schiavini, E. Santus, and A. Bagnato. 2007a. Additional support for an association between OLR1 and milk fat traits in cattle. Anim. Genet. 38(3):308-310.

Khatib, H., V. Schutzkus, Y. M. Chang, and G. J. Rosa. 2007b. Pattern of expression of the uterine milk protein gene and its association with productive life in dairy cattle. J. Dairy Sci. 90(5):2427-2433.

Leonard, S., H. Khatib, V. Schutzkus, Y. M. Chang, and C. Maltecca. 2005. Effects of the osteopontin gene variants on milk production traits in dairy cattle. J. Dairy Sci. 88(11):4083-4086.

Li, S., E. B. Crenshaw, 3rd, E. J. Rawson, D. M. Simmons, L. W. Swanson, and M. G. Rosenfeld. 1990. Dwarf locus mutants lacking three pituitary cell types result from mutations in the POU-domain gene pit-1. Nature 347(6293):528-533.

Liu, X., G. W. Robinson, K. U. Wagner, L. Garrett, A. Wynshaw-Boris, and L. Hennighausen. 1997. Stat5a is mandatory for adult mammary gland development and lactogenesis. Genes Dev. 11(2):179-186.

Mullis, P. E. 2007. Genetics of growth hormone deficiency. Endocrinol. Metab. Clin. North Am. 36(1):17-36.

Nadesalingam, J., Y. Plante, and J. P. Gibson. 2001. Detection of QTL for milk production on Chromosomes 1 and 6 of Holstein cattle. Mamm. Genome 12(1):27-31.

Renaville, R., N. Gengler, E. Vrech, A. Prandi, S. Massart, C. Corradini, C. Bertozzi, F. Mortiaux, A. Burny, and D. Portetelle. 1997. Pit-1 gene polymorphism, milk yield, and conformation traits for Italian Holstein-Friesian bulls. J. Dairy Sci. 80(12):3431-3438.

Schnabel, R. D., J. J. Kim, M. S. Ashwell, T. S. Sonstegard, C. P. Van Tassell, E. E. Connor, and J. F. Taylor. 2005. Fine-mapping milk production quantitative trait loci on BTA6: analysis of the bovine osteopontin gene. Proc. Natl. Acad. Sci. USA 102(19):6896-6901.

Svennersten-Sjaunja, K. and K. Olsson. 2005. Endocrinology of milk production. Domest Anim. Endocrinol 29(2):241-258.

Tuggle, C. K. and A. E. Freeman, Inventors. 1994. Genetic marker for improved milk production traits in cattle. Iowa State University Research Foundation, Inc., assignee. U.S. Pat. No. 5,614,364.

Viitala, S., J. Szyda, S. Blott, N. Schulman, M. Lidauer, A. Maki-Tanila, M. Georges, and J. Vilkki. 2006. The role of the bovine growth hormone receptor and prolactin receptor genes in milk, fat and protein production in Finnish Ayrshire dairy cattle. Genetics 173(4):2151-2164.

Weller, J. I., Y. Kashi, and M. Soller. 1990. Power of daughter and granddaughter designs for determining linkage between marker loci and quantitative trait loci in dairy cattle. J. Dairy Sci 73(9):2525-2537.

Woollard, J., C. K. Tuggle, and F. A. Ponce de Leon. 2000. Rapid communication: localization of POU1F1 to bovine, ovine, and caprine 1q21-22. J Anim. Sci 78(1):242-243.

What is claimed is:

1. A method for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo by i) obtaining a nucleic acid sample from a cell of the embryo, ii) determining the identity of the nucleotide of a position of the POU1F1 gene of the cell corresponding to position 10793 of SEQ ID NO:1, and iii) comparing the identity to the nucleotide to that of position 10793 of SEQ ID NO:1, and terminating pregnancy if said developing embryo does not have A at the position of the POU1F1 gene corresponding to position 10793 of SEQ ID NO:1.

2. A method according to claim 1, wherein pregnancy is terminated if the embryo is not homozygously A at the position of the POU1F1 gene.

3. A method for selectively breeding dairy cattle, comprising selecting a bull that is homozygously A at the position of the POU1F1 gene corresponding to position 10793 of SEQ ID NO: 1 and using its semen for fertilizing a female animal.

4. The method according to claim 3, wherein the female animal is in vitro fertilized.

5. A method according to claim 3, wherein MOET procedure is used.

6. A method according to claim 3, wherein said female animal is also homozygously A at the position of the POU1F1 gene.

7. A method for selecting a dairy cattle animal for its longevity or milk production trait, or both, comprising i) obtaining a nucleic acid sample from a cell of the cattle, ii) determining the identity of the nucleotide of the position of the POU1F1 gene of the cell corresponding to position 10793 of SEQ ID NO:1, and iii) comparing the identity to the nucleotide to that of position 10793 of SEQ ID NO:1, and selecting the cattle if the cattle is homozygous for A at the position of the POU1F1 gene corresponding to position 10793 of SEQ ID NO: 1.

* * * * *

SEQUENCE LISTING

<160> NUMBER OF SEQ ID NOS: 11

<210> SEQ ID NO 1
<211> LENGTH: 15952
<212> TYPE: DNA

<213> ORGANISM: Bos taurus

<400> SEQUENCE: 1

```
ttctccgttt ctattctttt gtgggaatga gttgccaacc ttttacttcg actgatacct      60
ttatacctct gaattctgag tcttctgcaa ctctgcctct gataatgcat cccagtgctg     120
cggagtgcct accggtctcc aaccacgcca ccaacgtgat gtccacaggt actaacttca     180
ataacagtct acatgcggct gcgccttaag atatcaggat gggtgctttg aatcttgcta     240
gtttagaatc tcattttaaa aaaaatttta atgtgtatta agttaaatat tcaggatatt     300
aaagaagaca aaatgcctaa gaaaatattc aagaaatatt agtaagtgta gtaatttcaa     360
gtattgttga ttttattata aaacctgtct tctatacaag taaacagtga gtctgaaaac     420
cactctatgc aaacatgtat gcataaagag taaaactaaa aaaatagtgt aaaataattt     480
aaaaggtgat ttttttttcct cttagagatt tatttggttt ttagattaca tttactacca     540
tgtctaaaaa atgccgtaca cctctgagta aacacaactg aatgattcct gataccaaca     600
acagtgggtt tcaaagaata aaataattag atgtttaaat acactttatt cagatggtaa     660
agaatctccc tacaatgcag gagacccagg tctgatccct gggtcaggaa gatcccatgg     720
agaagggaat ggcaacccac tccactattt ttgcctggcg aagtccaagg acagaggagc     780
ctggcaggtt acagtccatg gggttgcaaa gagtcggaca caactgaacg actaacactt     840
tcactttaaa tacacttaac ttctttagaa taattaaaaa ctcagaaacc aagtctagag     900
gcaatataat atttatttgt ttatttttaa aactttttat tttatattgg agtatagcca     960
gttaacaatg ttgtgatatt tcagatggga cagcaggga attcagccat acatacacta    1020
tatcctttt tacccaaact cccctcccat ctaggctaga ggcaatataa tatttagaat    1080
ccatgaactg atttgaatct tttcaagatt tagttctgaa gagatttcaa cctttaatca    1140
agttttata ttttcttata aactttctt agatgaaaat taaaattaat tcaaatatat    1200
tgtctcaaac acaaccaagt aaataaatat gttttgttaa tgtgtctaat ttttactcag    1260
taacaaaggg ttttgattaa taaacaatgt cttgggtaaa tgtctgttta atagcacttt    1320
tcacttgtaa agcaatctaa atatgagcta aatttttataa atttaaaaat caatttgagt    1380
tgacacattt atatgccaat ttaaaatatt ttagccttat attttgttaa aattaagcag    1440
ctttgaaagt tatatgtaag tttggtatta atctttaaca gaattttcaa atatctgaag    1500
atcatattat ctagatttgg ggaaaattat taatgtagag atgtttttta tctactgaag    1560
agtctcagaa tttaattaaa catatgctga tgcaaatatc ctcaaacatg gttttaaaaa    1620
aaagtaataa agtatttta tgaagaggtg tggtataaat aaatttaaac aattatcaca    1680
tattgttgta ttgttcagtc gctaagtctg aactctgcaa ctctttgcaa ccccatggac    1740
tgcagcatgc cagacttccc tgtccttcac tatctcctgg actcttccca tacaattatc    1800
acatagctaa ttgtgtattt taaataatgg acatttaaat agattgagaa tgagaaggat    1860
agtgcatttt tgcataatat actgtatgtg gatagtattt ggctagaata aaaattggaa    1920
ttgaggttaa aattaagcag gtttaagctc aaaaccctat ttatttaaaa aaaaataaaa    1980
gtaaataaat aatgtatcta gtaaattagc ttgtcattta tatgacttcc ccaaatcagc    2040
aaaacaaaag aatttaaacc ttggaggtaa aaaaattcat aattagtaac aatgtcctaa    2100
atggctattg ttattgtttt aaatagcaat agcattgatt ctataatttc tccatcaaat    2160
tgtaaccgta tatatctaat tgtctaggta aagaattaga aatgattata atgagaggga    2220
aatggcaacc cactccagtg tttttgcctg gagaatccca gggacggggg agcctggtgg    2280
```

-continued

```
gctgctgtct atggggtcac acagagttgg acacgactga agcgacttag caacagcagc    2340
agcataatga gaggagcagt tggatattca atgcgtttca tgtttcttta attttggaat    2400
gcatagaaat tattataaca caaaattatt tcagttctat gtgtcagttg taaaatgaaa    2460
atttatacag atactttaaa atattaaaaa tgagttatag ttagagaaaa tgttttactt    2520
tatgtcttta attgatagac tacatatttt caaaaaggac tataaatctc ttctaatatc    2580
tcatattatt caagaagata caattatatt tttgaaaatc caccactcta ttcaggacat    2640
aatgggaaaa agtataaaat aagatataaa agaaaacatt gattagtgat tttattgtta    2700
gtagttcatt gtgattcatg ttgaaagctt gatagaagtt aagtaattca aatttaattt    2760
caaaatacac cttaattcaa tgatacttgt agctatttat aaatgaagtt aagttatatg    2820
ctggactcaa cctttataaa cctctagtta ctcagtgatc aatgaattta ttttttgacc    2880
agcttcatca ttagaattgt tcaattaatt gtgtgcatgc agaaaatcta caagctcatg    2940
gtttcaatac cagcctaaat acattgcaca ttgtcacaga gttttttgtaa gcctctgaat    3000
ttaatggagt tttatgatca tacccaataa aaggctagtg ctctgccac ttcctctttg    3060
atggaagaaa tttgttaggt gaatgagcag aagtaaaagt aaagacccat gaagagttga    3120
tttctgtatt cattgctcca gcaaaagaca attttatggt accatgttat acgagaattt    3180
taagagacta ttctctggtc agttctttgc aaagtctaca ttgggtgaaa cctgcaagaa    3240
aactgcagct tccagttgtg tgcgtgtgct cagtcactca gtcatgtctg acacttggca    3300
acctcatgga ctgtagccca ccaaggttaa aactggtcag tcacgccaac ccagaacact    3360
ggatataatt aatgaaggct ctagtccact gtgatgattc atgaactcgt tacttgggaa    3420
aaatgtcaac ccctagtttt agcatactca tcagagaact gccccaaat gagaacaaat    3480
tattggcata taactttaag aatagcataa atgtgtacat ttgaaatgaa acgaatgtgt    3540
cttgaatcct catacatttt cttaccagtc ccgtctattt tgtctttgat ccaaactcct    3600
aaatgtttgt gcacatgttt tgtggtgaca atgctgggaa acacagcaac aggacttcat    3660
tattctgttc cttcctgtca ttatggaaac cagtcatcga cctatggcgt gatggcaggt    3720
aagaaaaatt gtctttacat gtaagattga gtttggggac gcttggatgc attttctggg    3780
tcgaagggaa tcttgaccag agtgtatcat gaaattcaga tctcctaacc ttagaaattg    3840
ctgctaaatc caccacttac tataatggtc cctgatctgt aacgccttca gagatcataa    3900
tagttatacc tgatcactgc tgttctccac atgcctgaaa tgaactgcta tgcttcttaa    3960
cgcctgtgtt tgctttgtat gatttttatt ctaattctct gttgccaaac tgctaattgt    4020
cacttgctta tgccattggt gggcttgcct ccagtaataa taaggtagct gctagcctta    4080
tgtaactatt taaattttaaa agtaaattaa ctaaaataag gtcagattta aaattcctca    4140
gttgccaaca gtgagcaagt cagcaaaagc tttaaatgac ttcattgccc gcctccatac    4200
caacagggtt aatgattatg aggtacggaa cttaatagtc atcatttccc ttgagatttt    4260
ggctgttcct tcagttcctg aatttaaaat aaaacaggaa agtgcttaat aatcttttgt    4320
ggctaccaaa gcagatagac taacttatag agcatattcc tcatcacagt atttcttttg    4380
gccatttggt ctgtaaagat aaataagaca ttgaaggcta agagagattt gcagcaactt    4440
tagccatagt tgaatccttg gcagcccgtg ctgagatgct ctgagtcttg gataagattg    4500
aaatagtata agttacatac ttatttccct ctggataaag aaagcatcac tatatcaaga    4560
taaactatct tgtttgctga cacttaaatg aaagtattgt tagcaacttt cttaagggaa    4620
agaaaatctg acgtaagaga tccactcatc acaaaatta tgacttaatt ttagaccatg    4680
```

```
gctatacagt aatttttttg tgcacagaaa ttatttagaa atctcaatct tttatattta    4740
tttctgcagc aagaaataat ttcagtgaca ataaactact aatgttctat gtgaaaaata    4800
taaacgtgtg tgtgtgcatg ctcgtgtaat agttgttatc caagtaggta attaaaaaat    4860
caaacataga tttatgccta taaatttgaa attaaattga acaaagaatt tagttcacca    4920
acctttaatt tctaaaaatt tctcaaattt acactaaata aaacattaaa actttaaaat    4980
aatatattct agaacaaatt agcttttcct acattctgtt agagagcatt ctgaataaac    5040
ttatatcctc acctttatga tgaagtgaaa actgatgttc ttaatggtta cctttaaatc    5100
ttaatgtctc tcttcaataa ttaaaaaata aggaaagtca tattttcctt cctctgtgaa    5160
aacggaccgt ttatgattcg tgtacttagc tgttaatcag tatccatggt taatgagagg    5220
atctctcgtt gaagatgaac tactttcatt atagaaatag tagaacaatg tgcatttagc    5280
cactagcggt gccgctcaaa tgctttctgt ggcctccacc acacttggat tacagagaca    5340
agaaatgatg agtttataga catgtgctac tctttcttgg aggagagagt ccttgctgtt    5400
ccttcacagt agttcccagg aacccacatg caacttaagt catctctgca cccagcaagg    5460
ggcagcaatg agtggaggtt agtgctcaga ccaaacactg tgagatgatt tttactacta    5520
cctccctccc accagatcta ggtagaagct gctgagttca cagctggcct gagaaacctg    5580
acttccttcc tgtttccagg gttgcaggta acaagcccag gttcacactg agagtccaca    5640
ggcaactcag gttgtgctgg tccaagtttc ctcagcaggc cctcagcaaa ctttcatctc    5700
cattagaagt taaaaaggag aggtctttgg aaaaacctttt taaaatgatt caaagcccag    5760
gttggtgata ataatgaaaa aaatggatgt cctaagcttt ggaggtattg ctgtagtctt    5820
aaaccaaaat tacatatatt ttgtcgctga aagaaaaatt caccatgtca agcatagaga    5880
ttatatttga atattttga gagggagatc attaaaatgt gatgtgcttt gtaatttgtt    5940
acaatgtcac tattttgaca tatattcagt attagccttt gcatcacggc agatttaatc    6000
tcagagaatc tgaacctttc tgctgtcatc cccagagaag ctacacaaat tgagtcataa    6060
aacacaggga ttcagaatat tcaggaattc acaaaaggtt taaaatacac aagagaaacc    6120
tgataatgtc atttgaattt tctgagaagt ctcaggcgtt catcaaatca gccacttcca    6180
cacaatccac agaagcgtct aatcaccaac aacgaaggtt cattgtcaca tactccatat    6240
aaaagtgaag ctgcacaaag agcaatattt caaagggtgt gaaattgctt tatttgaata    6300
tggttatttt atccctatac tctgatgctt atatgtagtc tgagcatttc attaaattaa    6360
taactcactg gaaagcaaga gctacagctc atattttaag ctaaggttgg taggaaggat    6420
tctaatcatc agatgaatcc tctgtacctc atagtccagg tgtggggata tcaaagagaa    6480
tgattggtgg ggtgaaatga attagccaca ccaggaacta attacaaacc tcgttcaagt    6540
tagcatctca aagtgttagt ctcttcacat ccaagttgtg atgggtacca tacatagctc    6600
tatctgagtt gagttgtggc agcttttctac caacttagcc tggttttctc cttgatcttc    6660
tcttcagata cattcatagt taaatttctt cttctgtttc ttctctccta agtacttaaa    6720
taattcaaca gcctgcagga tggataatag gaaacaggga attacaaata ctattcaaaa    6780
atctcttcta gataaacacg aaagaaaact aataacaaaa acctttcaaa attctgattt    6840
ctgggtatac aaggtggtgt ctgttctcat ttgtaaagct gggtgaaagt tggaaaacaa    6900
acttaatgag ctgtgtacct tgcccgccgt cctgtgtgaa ctgggctaat cagctacatg    6960
gtaatgattg ctaaacccag caaggttatg tgttttaatg gccacccaag gtgtgcagta    7020
agagtccttg attaaaaatt gatcttaaga ggaaagcaaa atagctgatg ttggaaaatt    7080
```

```
attcaaggag atgaatgctc tttttaaatg agatgtgaat aataagaata aagatgaat       7140
atagctaaaa agtgtctttt ccacctgggc taggacaaga ggtaccagaa atatgtttca      7200
catttacata ggcaaacagt ctactttgga ggccatctct tcattcttaa attgtctttt     7260
ttctatttcc ttttttcttt ttttgtttta tttagtttta tttttgcctc acttattctg     7320
gatgtgttga cactaaggga aggagtaatt ctgaccatct tttgcctctg gatcatgaaa     7380
ggcgcctgca gtagcatgga cactgtgtat tattccttaa attatgtagc atctgtctca    7440
acttcacaac tcaaaagcag ctacaggcaa tctgtaaaca aatggccatg ctgtgctcc     7500
aaatcaacct aatttacaga actaggcaga agacctgttt atatgtggat aggatgtagc   7560
aatgcacaaa agagaaaaaa aatcacaatt caaatttatg atttgtttca cattgtcatg    7620
catgaacgta aaaaagaaa ataaatggaa atatttaaat gaactgtgct gtgcatctct     7680
acagcaaggt gggggtattt tactatatcc ttcttcccct gtttgttctt ttaaagcttc    7740
tagctcacaa cctcagagat gttgtcagtt agcagctgtc tgagccacgt gctgcagaaa   7800
agcagtgtgc cctgtatcat gggaccttga atcaggtgcc cgtaaggcat gctggacctc    7860
agcttcccat cttctgcttt taaagattta atctctgttc ctctccctcc tctgccgtcc    7920
agaagtccat gcagagcagt tcagagaggc tatggtggat taatctgcag ggtgaaaatc  7980
catcttggac tgtaaagaat gtacaaacct ttccaagcta tttaggtgtg cacttgttct   8040
aggcttatag acaagtttgg tttatcagtg ttttggaaaa tattcatgaa acttctgtgg   8100
cacacaactt cctgcatctt ttctctccgt gctcaaaccc cgacttctta atattccagg    8160
ctttagaaaa acctttttaaa ataccttgtc acatatacca taccaatcaa tccccatttt  8220
ctcccaaata caggatcata taatagaaat cagtttgtct gaccatgctt gtgactgtcc   8280
caaatttctg tttaacatta gtttcaggaa aactgtgtcc ctgtggataa ttgtggatac   8340
tttcagttaa tgaaaaataa cgcagcacac atcgtgtttt ccttcctcct ctagatgcca   8400
aacttttgaa catggtattt cttgtgcact ctttatgaac tcatgttcaa atttattttc     8460
taaatgtcca tttctccaga gtatttataa agtatacact agctttaaat ttttccataa   8520
atagagatgg cacacttcca atattttttgt aaatatttat aaaactttttg tttgaaagca  8580
tttgtttaat gtgaccaaat atatttaaga tgcagaatct ttgagtcatc tgatttccct    8640
gagtacagat tacctgaaaa atgaactgat tattgatgtg gcctattgag gtattcacag  8700
ggcttcactt ctagtttcaa ttgtatagtg aattcatctt agcactcaag gaacgttatt    8760
tgttttata tgaattttaa attgtggata aaaaaataca cactttttttc tctgaaaata  8820
aaacaaaagt ccttagataa atattaagta aatgttaaca taaaggtgat aaatttttt     8880
atatattagt attttactta actagtagaa atctaaaact aacattaggc caaaaatgag   8940
ctttgttaaa atgtaacaaa cattaaaaaa attgaattttt gtaataaatt aaaaattgat  9000
aaaattgctt tttaaaattg tatctggtct attcaatgta gcacccacta aagcaaaaag   9060
tggatgatta acaataacaa caaaaaactg atagttttg atttttgaaa gtaatatgaa    9120
ttgctttaga cagaaatagt ttcttttgta tgtttttttat atccatgaaa cagctatact  9180
tattttatga tattttgctt aatttctcac ttgtatgtat tttgtttcag aaacataata   9240
gtctactgga taggggtaca cttcaaaatt atattttctc atataaataa tatgagccaa  9300
caacttactg acttgcaata ttctttgctc attacatatt gatatattaa tttaagattt  9360
atatattctg gcaaaataca ctattactca tgtctgattt ctgactgtat ttatagaaa    9420
attataaata gcataaaact gatgtatttt ttagtaagtt tctaagaatg attactgcct   9480
```

```
attttctata gtcatttata tttaatttat actcataaga aaaatgatta attattgaat    9540 atttttattta tatcaaaatg tcttggttat acccatgtca tttaatataa agtgaaatcc   9600
ttatgaataa aaatgtaata tactgctgaa gaaaacagaa ataaaatgtg tgggaatttg    9660
gcttatacca tcctgtcacc aatactccct gactgagatt ctctcttctt tccaaatgaa    9720
gaatgaaatc tagaagcaat taaacaatta aatcatgtag ttttttgaga tttctcattt    9780
aactaactca atggattcag tgcttcatca tttatgaggg attatgtatt gtatctcaga    9840
gaaggaaatg gcaactccag tattcttgcc tggagaatcc cagggacaga ggagcctgtt    9900
gggctgctgt ccatggggtc gcacagagtc ggacacgact gaagcgactt agcagcagca    9960
gcagcagcat gtatcatatc tagaattgca cccttccttg acacttaact tttctcttctt  10020 aaatagtaat caagaaatga ttccatcata gtatattttg caagaatctt gttgctgacc   10080
ttctaataga tcttaaaag ttacttttg tcgacatcca tcattaccat aaatctatt     10140 taaaccttat taatgtattt tttgttctca taattttcgt tttacttgcc tttactaaat   10200
taagcattta ctgataaaac attggatttc ttaatgctgt aaaatcaatt tttcaatgct   10260
atgaaaattt cccagaatag cacttaacat acaccttgat tataattaag aaaatataca   10320
ttctggtaga gttgaacctc agattcacaa taacaaatga aaagattttt gtttgttttt   10380
ggggagccat gctgaattcc ataaccagga atcaaaccca tgccctctat actgaaagga   10440
tgaagtctta accactggac tgctatggaa gtcttttaag agaaaaacaa tgatggaaaa   10500
ctcacacttt tttgaaattt gcttattct atttaaatta tttgcaagtc cctggttctt   10560
tcctttggct ttgcattatc tttgtttcca ctgctcccag gaaggtggaa aaaaagatc   10620 ctatttatac taagctacac tgacttctac ttcagaaaag caaatgtcag gtaacctttt   10680
agaactgaga ctggctgtca cagaacaatc tgatgggcca aaattttcca tgtatcaaaa   10740
tgagggataa ttacaaatgg tccttttctt gttgttacag ggagcttaac cccttgtctt   10800
tataagtttc ctgaccacac gttgagtcat ggttttcctc ccatgcatca gcctctcctt   10860
tcagaggacc ccactgccgc tgatttcaag caggagctca ggcggaaaag caaattggtt   10920
gaagagccaa tagacatgga ttctccagaa atccgagaac ttgaaaagtt tgccaatgag   10980
tttaaagtga gaagaattaa gctaggtagg tgcttgttaa cagctgtggg acacacaact   11040
ccgtctgcaa agtcttactc tattactgtt taatctctta catgctgctc agaagtctaa   11100
gacagttctc attctacatc tctactgtgg atgtaagttg aattatgaaa acctatagca   11160
accttcattt ccttgtaaat tcttagcagc aaaaatatat agattctaa attaatggtc    11220 tcctttcaa acataagttt agaaatacct ttgtttatt tgaattaata cctttgtgtg    11280
attcaaaagc taaaagctg tgagaattgt atccctctgc ttatccttcc tgtttatcag    11340
tgttattagt ttctgtgaat ccttctattc tatgcatatt catataagca aattcatgta   11400
tttcttcata tagacatttt tcatttgact attttggaga gctttcagta ttagtttttt   11460
agagagctct tctttttaat gcatctctca attccatttt atgaatatat taccagtctc   11520
ctactgatgg aatttagatg gtcttcaatc ttatgttact gaagacaatg atgcaatgat   11580
taacttcata aatagcattt tgcaccgata aaaatatatg tgcagggaaa gtgttaaaag   11640
caaaattgtt tgattgaaga gcatgtgtat ttgtaatttc agtagatgtc aaattggtct   11700
ctatgtaaat tctaacaaat cttattgcca ccatgagtat ctcctttgcc actcttcaga   11760
atatgaattc tgttaaggca gaagtttttt gttttttgtt tatttccttt gctttctcct   11820
taatggcata tcctcagcac ttggaacagt gactggcatg tagaataaaa aatagttatt   11880
```

```
gaagggaaaa gatgctatta atcttttgga cctttgcaaa tcagttaggt gaaagtagca   11940
gtttcatttt aaatttccct tatgagtgaa gagtgaaaga agttttttcat gtgttggaca  12000 gtcatttgta attccttttc tgtgagcgat ctgttcatag cctttgctca ctttctaggg   12060
tgaagtgttt ttaatgtaaa taatcataat aattaaccct gatttaaatg catgaaatat   12120 attttaatg gattgaactg atagtacaaa cttctgcatt tgtggactga gccattggta    12180
acttttaatg atatcaattg atgggcatca tatgtaatca ttttatgcat acaggtatat   12240
agccttgggc cctgaattaa tatgtagtta ctgtttgtca taaacacagc agtaggcatc   12300
tttatgacat tcatttttcaa tttactttt atatgactgt gaatgtttca aattctacat   12360
tgatgacatt tgtcaactta tattctgaga atgtttgaga caatctatga aaacttttg    12420 cctggagata gaagcattac caaatgatat aataaatgct tggtgatata cataaaatgt   12480
tgtgtgacca aagtctcata ataagcatgc ttttagggaa agtaaacaca gttcttagtt   12540
ttatttgtta acttcaacat gttgaatttt tcactcttac agctgagata aaaatatttg   12600
tgatatatca ccatatagtt tacatattat attttaatat ctatagattt tgagcatatt   12660
tcaacagatg cctaataata atgattagag agaattttta aatgtcttct aaagtgtgta   12720
ttaaggattc cctggtagaa cagctggtaa agaatccacc tgcaatgcag gacacccag    12780 ttcaattcct gggtcaggaa gatcagttgg agaagggata ggctacccat tccagtattc   12840
ttcggcttcc cagtggctca gctgttaaag aatctgcctg ctatgaggga gatctggatt   12900
cagtccctgg gttgggaaga tcccctggag atgggaacag ctacccactc cagtattctg   12960
gcctggagaa ttccatgtac tgtatagtcc atggggttgc aaagaatagt ctgactacac   13020
ttatattagg ttataaaaat gattcatgta taattactac agtatatagc acagtggcaa   13080
aaaaataaat ctggatacat taaaagaat catttcacta ctttatacct atgctacatt    13140
gtctagaaac ttttcttata tattttttgca aagtgtgttt aacacattta tccagttttgg 13200 ctaaatatga atggcagatg ttcctatctg aattcttttg gcttctaaaa tattaactta   13260
ttaactagaa ggaatttttt aaaatactag acaattctac actgcataac cttactgtta   13320
ttctaaattg ctaacaaatt tatcgttaaa agcaatattt aatagttgac aaaaatacta   13380
cacaaattta tacaatagtg gacccaaatc agtgtttctt gcaaaactga agctcatggc   13440 cttttgttatt ctttcacagg atacacccag acaaatgttg gggaagctct ggcagctgtg  13500
catggctctg aattcagtca acaactatc tgccgatttg aaaacctgca gctcagcttc    13560
aaaaatgcat gcaaactaaa agcaatatta tccaaatggc tggaggaagc cgagcaagta   13620
ggaggtacaa aagctgtgtt tctggaaaca gtgatgtttt aacctaaaaa caatggtttc   13680
cctcagttga atttgtacta aagcaagagg tttgaagttt ggtttgattt ttctctttga   13740
catgaaaaat aagtatcttg tttcatcaca ctatgaagaa aagcaaggcc agtgaaagtg   13800
tagaaataaa tttattgaga aggtaaataa tgagagaata aaatatatag ggaaagtttc   13860
tacacaatgt ggcataggtg tgaagtggtg aaatgattct ttttaatgta tccagatttt   13920
ttcctgctgt gctatatact gtagtaatta ttcatgaatc atttttacaa cctaatataa   13980
gtgtagccag agcattcgca cacaccgttc tttctagtga atagcaagca attgctagat   14040
aaacaattta atgtgataaa aattatctac ttatattaat gtcaaggctg gctaaagagc   14100
aagatttgat agcatttaga gcaactgttt caacaaagat agggtatgat ttaaagacaa   14160
ctgttaatat ttataaagtt aatattttt tctgtgttaa cattttaatc tagggcttgt   14220
aatctaaaat gatgtatact gcaaatattt aaaacaaaaa tgtatggtaa ttctattttg   14280
```

-continued

```
tattgtttta taaagaaact ttaaatccaa atctgatagt taaaaaaaaa acctggtttg    14340 ttttgtaat tattcattgt tttcgcatca cagctttata caatgagaaa gttggtgcaa     14400
atgaaagaaa aaggaaacgg agaacaacaa tcaggtatac ttttgagata ttaagagtta    14460
gtggagaaga aaatgatatt ttacaaatgg aatgaacatt tgagtataat atagtttcaa    14520
tataacataa aaatgaatag agccaattga gaaaataggt gaaaaagcac aacattcaat    14580
aaattacttc tgagaaacag ctggaaattt aaaatttgat ggaaaaatat gtattgtttg    14640
attcaagaac agttttgctc tgcaagtttt ggataaaaca gaagctgtac aatcacagct    14700
aaaaagaatg actgtttcta ctgtgtcata atgtgttgat ttatgtttag acataaatct    14760
tgctccggga aagaccccat ggactgtagc ctacaggttc ctctgtccat gggattttcc    14820
aggcaagaat aatggagtgg gttgccattt ccttctccag gagatcttcc cgacccaggg    14880
attgaacccg atctcctac attgtaggca gatgctttac catctgagcc acaagggaag     14940
tcatctatct atattatttc aaattaacaa aactggtcac tagtatttta gttgcttaaa    15000
gttcaaaatg acttctagca tttcaagcca gattgttcat ttatcttttt gtagtttccg    15060
tgaggctcat ggaggaattg ctaatataca ggttttgttt tggttggtta gttgtacact    15120
aaacatttca ataacctgag ttctggggga catttagaaa tgcatacaga attattttct    15180
tctcagtaag tcagtgccct cttgtggcag aaagtggata acaatgtcg gggttccctc     15240 cttaatttct tcctgtgact ctggtaaaag gagcctacat gagacaagca tctaaatgtt    15300 caaaaaact tcacatttat tattgttgaa aagctttgaa ggtgttttca gtgtctttag     15360
gtttcctttt tacgttaatg ttagtactaa tatttaggaa atgtaaccta acttgatttt    15420
gatgggccta aaccatcatc tcccttcttt cctgccaact cctcacctcc cagtattgct    15480
gctaaagacg ccctggagag acactttgga gaacagaata agccttcctc tcaggagatc    15540
ctgcggatgg ctgaagaact aaacctggag aaagaagtgg tgagggtttg gttttgtaac    15600
cgaaggcaga gagaaaaacg ggtgaagaca agcctgaatc agagtttatt tactatttct    15660
aaggagcatc tcgaatgcag ataggctctc ctattgtgta atagcgagtg tttctacttt    15720
tcattccttt ctcttctcca gccaaaatag aaattagtta tttggttagc ttcaaaaaat    15780
cacatcagta attttgcag aagtgtttct tttctacttt aaaaataaat acaatttaaa    15840
ttatgttgat gaattattct cagaaggcac attgtacatt ttaagccaaa gactaatagg    15900
attcaaacaa tgattctgtc cctttcacta tatctttccc tctatctctc cc            15952
```

<210> SEQ ID NO 2
<211> LENGTH: 39
<212> TYPE: DNA
<213> ORGANISM: Artificial Sequence
<220> FEATURE:
<223> OTHER INFORMATION: PCR Primer 1

<400> SEQUENCE: 2
caaatggtcc ttttcttgtt gttacaggga gcttaaggc                          39

<210> SEQ ID NO 3
<211> LENGTH: 25
<212> TYPE: DNA
<213> ORGANISM: Artificial Sequence
<220> FEATURE:
<223> OTHER INFORMATION: PCR Primer 2

<400> SEQUENCE: 3
ctttaaactc attggcaaac ttttc                                         25

<210> SEQ ID NO 4
<211> LENGTH: 72
<212> TYPE: PRT
<213> ORGANISM: Mus musculus

<400> SEQUENCE: 4

Ser Ala Ala Glu Cys Leu Pro Ala Ser Asn His Ala Thr Asn Val Met
1               5                   10                  15

Ser Thr Ala Thr Gly Leu His Tyr Ser Val Pro Ser Cys His Tyr Gly
            20                  25                  30

Asn Gln Pro Ser Thr Tyr Gly Val Met Ala Gly Ser Leu Thr Pro Cys
        35                  40                  45

Leu Tyr Lys Phe Pro Asp His Thr Leu Ser His Gly Phe Pro Pro Leu
    50                  55                  60

His Gln Pro Leu Leu Ala Glu Asp
65                  70

<210> SEQ ID NO 5
<211> LENGTH: 72
<212> TYPE: PRT
<213> ORGANISM: Rattus rattus

<400> SEQUENCE: 5

Asn Ala Ala Glu Gly Leu Pro Ala Ser Asn His Ala Thr Asn Val Met
1               5                   10                  15

Ser Thr Ala Thr Gly Leu His Tyr Ser Val Pro Ser Cys His Tyr Gly
            20                  25                  30

Asn Gln Pro Ser Thr Tyr Gly Val Met Ala Gly Thr Leu Thr Pro Cys
        35                  40                  45

Leu Tyr Lys Phe Pro Asp His Thr Leu Ser His Gly Phe Pro Pro Leu
    50                  55                  60

His Gln Pro Leu Leu Ala Glu Asp
65                  70

<210> SEQ ID NO 6
<211> LENGTH: 72
<212> TYPE: PRT
<213> ORGANISM: Homo sapiens

<400> SEQUENCE: 6

Ser Ala Ala Glu Cys Leu Pro Val Ser Asn His Ala Thr Asn Val Met
1               5                   10                  15

Ser Thr Ala Thr Gly Leu His Tyr Ser Val Pro Ser Cys His Tyr Gly
            20                  25                  30

Asn Gln Pro Ser Thr Tyr Gly Val Met Ala Gly Ser Leu Thr Pro Cys
        35                  40                  45

Leu Tyr Lys Phe Pro Asp His Thr Leu Ser His Gly Phe Pro Pro Leu
    50                  55                  60

His Gln Pro Leu Leu Ala Glu Asp
65                  70

<210> SEQ ID NO 7
<211> LENGTH: 72

-continued

```
<212> TYPE: PRT
<213> ORGANISM: Chimpanzee

<400> SEQUENCE: 7

Ser Ala Ala Glu Cys Leu Pro Val Ser Asn His Ala Thr Asn Val Met
1               5                   10                  15

Ser Thr Ala Thr Gly Leu His Tyr Ser Val Pro Ser Cys His Tyr Gly
            20                  25                  30

Asn Gln Pro Ser Thr Tyr Gly Val Met Ala Gly Ser Leu Thr Pro Cys
        35                  40                  45

Leu Tyr Lys Phe Pro Asp His Thr Leu Ser His Gly Phe Pro Pro Leu
    50                  55                  60

His Gln Pro Leu Leu Ala Glu Asp
65                  70

<210> SEQ ID NO 8
<211> LENGTH: 72
<212> TYPE: PRT
<213> ORGANISM: bos taurus

<400> SEQUENCE: 8

Ser Ala Ala Glu Cys Leu Pro Val Ser Asn His Ala Thr Asn Val Met
1               5                   10                  15

Ser Thr Ala Thr Gly Leu His Tyr Ser Val Pro Phe Cys His Tyr Gly
            20                  25                  30

Asn Gln Ser Ser Thr Tyr Gly Val Met Ala Gly Ser Leu Thr Pro Cys
        35                  40                  45

Leu Tyr Lys Phe Pro Asp His Thr Leu Ser His Gly Phe Pro Pro Met
    50                  55                  60

His Gln Pro Leu Leu Ser Glu Asp
65                  70

<210> SEQ ID NO 9
<211> LENGTH: 72
<212> TYPE: PRT
<213> ORGANISM: Canis familiaris

<400> SEQUENCE: 9

Gly Ala Ala Glu Cys Leu Pro Gly Ser Asn His Ala Thr Asn Val Val
1               5                   10                  15

Ser Thr Ala Thr Gly Leu His Tyr Ser Val Pro Ser Cys His Tyr Gly
            20                  25                  30

Asn Gln Pro Ser Thr Tyr Gly Val Met Ala Gly Gly Leu Thr Pro Cys
        35                  40                  45

Leu Tyr Lys Phe Pro Glu His Gly Leu Gly Pro Gly Phe Pro Ala Ala
    50                  55                  60

His Gln Pro Leu Leu Ala Glu Gly
65                  70

<210> SEQ ID NO 10
<211> LENGTH: 20
<212> TYPE: DNA
<213> ORGANISM: Artificial Sequence
<220> FEATURE:
<223> OTHER INFORMATION: PCR-RFLP primer 1

<400> SEQUENCE: 10
atactcatca gagaactgcc                                             20

<210> SEQ ID NO 11
```

```
<211> LENGTH: 20
<212> TYPE: DNA
<213> ORGANISM: Artificial Sequence
<220> FEATURE:
<223> OTHER INFORMATION: PCR-RFLP primer 2

<400> SEQUENCE: 11
cattaaccct gttggtatgg                                                   20
```